US012193873B2

(12) United States Patent
Aase et al.

(10) Patent No.: US 12,193,873 B2
(45) Date of Patent: Jan. 14, 2025

(54) SYSTEM AND METHOD FOR DISPLAYING POSITION OF ULTRASOUND PROBE USING DIASTASIS 3D IMAGING

(71) Applicant: GE Precision Healthcare LLC, Wauwatosa, WI (US)

(72) Inventors: Svein Arne Aase, Trondheim (NO); Andrew Gilbert, Oslo (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 29 days.

(21) Appl. No.: 17/575,141

(22) Filed: Jan. 13, 2022

(65) Prior Publication Data

US 2023/0218265 A1 Jul. 13, 2023

(51) Int. Cl.
*A61B 8/00* (2006.01)
*A61B 8/02* (2006.01)
(Continued)

(52) U.S. Cl.
CPC ............... *A61B 8/12* (2013.01); *A61B 8/02* (2013.01); *A61B 8/42* (2013.01); *A61B 8/466* (2013.01);
(Continued)

(58) Field of Classification Search
CPC .... A61B 8/12; A61B 8/02; A61B 8/42; A61B 8/466; A61B 8/483; A61B 8/5207;
(Continued)

(56) References Cited

U.S. PATENT DOCUMENTS

| 6,122,538 A * | 9/2000 | Sliwa, Jr. .............. A61B 8/483 600/407 |
| 2008/0269611 A1* | 10/2008 | Pedrizzetti .......... G01S 7/52071 382/128 |

(Continued)

FOREIGN PATENT DOCUMENTS

| WO | WO-2013121431 A1 * | 8/2013 | ............. A61N 1/365 |
| WO | WO-2015024110 A1 * | 2/2015 | ........... A61B 5/0037 |
| WO | WO-2020212551 A1 * | 10/2020 | ........... A61B 8/0883 |

OTHER PUBLICATIONS https://www.youtube.com/watch?v=j0z4FweCy4M.

*Primary Examiner* — Joel Lamprecht
*Assistant Examiner* — James F McDonald, III
(74) *Attorney, Agent, or Firm* — Boyle Fredrickson S.C.

(57) ABSTRACT

A system and method is provided for obtaining ultrasound images of an interior of an object that includes an image processing unit that receives and processes acquired ultrasound scan data to create ultrasound images derived from ultrasound image data, a motion detection system configured to detect a pattern of inactivity time frames within movement cycles of the object and an ultrasound imaging probe operably connected to the image processing unit to acquire the ultrasound scan data for use by the image processing unit to form the ultrasound images. The motion detection system detects a pattern of one or more inactivity time frames within a first cycle of movement of the object, obtains ultrasound volumetric scan data of the object during the inactivity time frame within a second cycle of movement of the object, and calibrates a location of a scan plane of the ultrasound image within the volumetric ultrasound image.

19 Claims, 4 Drawing Sheets

(51) Int. Cl.
*A61B 8/08* (2006.01)
*A61B 8/12* (2006.01)

(52) U.S. Cl.
CPC ............ *A61B 8/483* (2013.01); *A61B 8/5207* (2013.01); *A61B 8/5238* (2013.01); *A61B 8/5276* (2013.01)

(58) Field of Classification Search
CPC ................ A61B 8/5238; A61B 8/5276; A61B 8/4245; A61B 8/463; A61B 8/0883; A61B 8/4254; A61B 8/54
See application file for complete search history.

(56) References Cited

U.S. PATENT DOCUMENTS

| | | | | |
|---|---|---|---|---|
| 2012/0022843 | A1* | 1/2012 | Ionasec | G06T 13/20 |
| | | | | 703/11 |
| 2012/0123493 | A1* | 5/2012 | Anderson | A61N 1/3682 |
| | | | | 607/17 |
| 2017/0169609 | A1* | 6/2017 | Somphone | G06T 19/003 |
| 2019/0142392 | A1* | 5/2019 | Carolus | A61B 8/5253 |
| | | | | 600/437 |
| 2019/0162808 | A1* | 5/2019 | Rehwald | G01R 33/5676 |

* cited by examiner

SYSTEM AND METHOD FOR DISPLAYING POSITION OF ULTRASOUND PROBE USING DIASTASIS 3D IMAGING

BACKGROUND OF THE INVENTION

The present disclosure relates to ultrasound imaging, and more specifically to a method and system for obtaining and providing a 3D navigation volume to identify a current 2D scan plane during a 2D scanning procedure.

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

In various applications, the acquisition of one or more standard scan planes and/or views may be performed to provide a medical diagnosis. For example, a transthoracic echocardiogram may involve acquiring ultrasound images that include a number of standard views, such as a four chamber (4CH) view, a two chamber (2CH) view, an apical long axis (APLAX) view, a parasternal long axis (PLAX) view, a parasternal short axis (PSAX) view, and the like. To acquire the desired standard views, an ultrasound operator may manipulate the probe to an image acquisition position, such as in one of a suprasternal, an apical, a parasternal or a subcostal window relative to the heart. The ultrasound operator may manually rotate the probe to different rotational positions, such as between the PLAX and PSAX views, and/or move the probe into different positions to acquire the different standard views.

However, in positioning the probe to obtain these views, the manual rotation of the ultrasound probe may cause the probe to inadvertently glide away from the particular window, making it difficult to obtain the desired ultrasound image/view. The reasons for this can include that the probe is rotated and/or moved to a position partly covering ribs of the patient, the similarity between adjacent views in a particular window, e.g., the similarity of different PSAX views, and/or due to the inexperience of the operator in determining the proper probe position for the necessary scan plane to obtain the desired view. As a result, on many occasions the actual 2D scan plane can differ from the desired 2D scan plane, resulting in an image that does not show the required structures for an accurate diagnosis, e.g., when the position of the probe is not aligned with the true apex of the left ventricle of the heart, resulting in apical foreshortening.

As an alternative to manually rotating and/or moving an ultrasound probe to individually acquire the ultrasound scan planes of the desired standard views, an ultrasound operator may acquire one or more full 3D ultrasound volumes of a region of interest, such as the heart. The standard viewing planes may subsequently be detected in the 3D volume and presented at a display system for analysis. The 3D volume negates the need for a proper positioning of the probe as the desired 2D scan plane can be selected relative to the 3D volume in order to obtain the desired image. Alternatively, the 3D volume can be used as a guide to direct the operator regarding the positioning of the probe to obtain the desired 2D image.

However, 3D ultrasound is more complicated and time-consuming to set-up. Moreover, the frame rate is usually much lower than in 2D or thin slab ultrasound, resulting in the physical resolution of an image plane being much lower. 3D ultrasound also records substantially more ultrasound data and much of this data is unused to perform the needed analysis.

As a result of these shortcomings of each of 2D and 3D ultrasound imaging, it is desirable to develop an ultrasound system and method that provides an operator with a navigation tool for the proper positioning of an ultrasound probe that does not require a complete 3D ultrasound scan of the object of interest, such as the heart.

Further limitations and disadvantages of conventional and traditional approaches will become apparent to one of skill in the art, through comparison of such systems with some aspects of the present disclosure as set forth in the remainder of the present application with reference to the drawings.

BRIEF DESCRIPTION OF THE DISCLOSURE

In one exemplary embodiment of the invention, an ultrasound imaging system for obtaining ultrasound images of an interior of an object includes an image processing unit configured to receive and process acquired ultrasound scan data to create ultrasound images derived from ultrasound image data, the image processing unit including a motion detection system configured to detect a pattern of inactivity time frames within movement cycles of the object, a memory unit operably connected to the image processing unit, a display operably connected to the image processing unit to present the ultrasound images to a user, an ultrasound imaging probe operably connected to the image processing unit to acquire the ultrasound scan data for use by the image processing unit to form the ultrasound images, wherein the motion detection system is configured to detect a pattern of one or more inactivity time frames within a first cycle of movement of the object, to obtain ultrasound volumetric scan data of the object during the inactivity time frame within a second cycle of movement of the object; and to calibrate a location of a scan plane of the ultrasound image within the volumetric ultrasound image.

In another exemplary embodiment of the invention, a method for determining a location of a scan plane for an ultrasound image of an object includes the steps of providing an ultrasound imaging system having an image processing unit configured to receive and process acquired ultrasound scan data to create ultrasound images derived from ultrasound image data, the image processing unit including a motion detection system configured to detect a pattern of inactivity time frames within movement cycles of the object, a memory unit operably connected to the image processing unit, a display operably connected to the image processing unit to present the ultrasound images to a user, an ultrasound imaging probe operably connected to the image processing unit to acquire the ultrasound scan data for use by the image processing unit to form the ultrasound images, wherein the motion detection system is configured to detect a pattern of one or more inactivity time frames within a first cycle of movement of the object, to obtain ultrasound volumetric scan data of the object during the inactivity time frame within a second cycle of movement of the object, to form a volumetric ultrasound image of the object, and to calibrate a location of the scan plane of the ultrasound image within the volumetric ultrasound image, obtaining ultrasound scan data using the probe, determining a movement pattern of the object for a first movement cycle of the object, determining an inactivity time frame within the movement pattern of the object, obtaining volumetric ultrasound scan data during the inactivity time frame in a second movement cycle of the object, generating a volumetric ultrasound image of the object from the volumetric ultrasound scan data and calibrating a location of the scan plane of the ultrasound image within the volumetric ultrasound image.

In still another exemplary embodiment of the method of the invention, a method for determining a location of a scan plane for a 2D ultrasound image of a heart including the steps of providing an ultrasound imaging system having an image processing unit configured to receive and process acquired ultrasound scan data to create 2D ultrasound images derived from ultrasound image data, the image processing unit including a motion detection system configured to detect a pattern of diastasis time frames within cardiac cycles of the heart, a memory unit operably connected to the image processing unit, a display operably connected to the image processing unit to present the 2D ultrasound images to a user, an ultrasound imaging probe operably connected to the image processing unit to acquire the ultrasound scan data for use by the image processing unit to form the 2D ultrasound images, wherein the motion detection system is configured to detect a pattern of diastasis time frames within a first cardiac cycle of the heart, to obtain ultrasound volumetric scan data of the heart during the diastasis time frame within a second cardiac cycle of the heart, to form a 3D ultrasound image of the heart, and to calibrate a location of the scan plane of the 2D ultrasound image within the 3D ultrasound image, obtaining ultrasound scan data using the probe, determining a movement pattern of the heart for a first cardiac cycle of the heart, determining a diastasis time frame within the cardiac cycle of the heart, obtaining volumetric ultrasound scan data during the diastasis time frame in a second cardiac cycle of the heart, generating a 3D ultrasound image of the heart from the volumetric ultrasound scan data, and calibrating a location of the scan plane of the 2D ultrasound image within the 3D ultrasound image It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
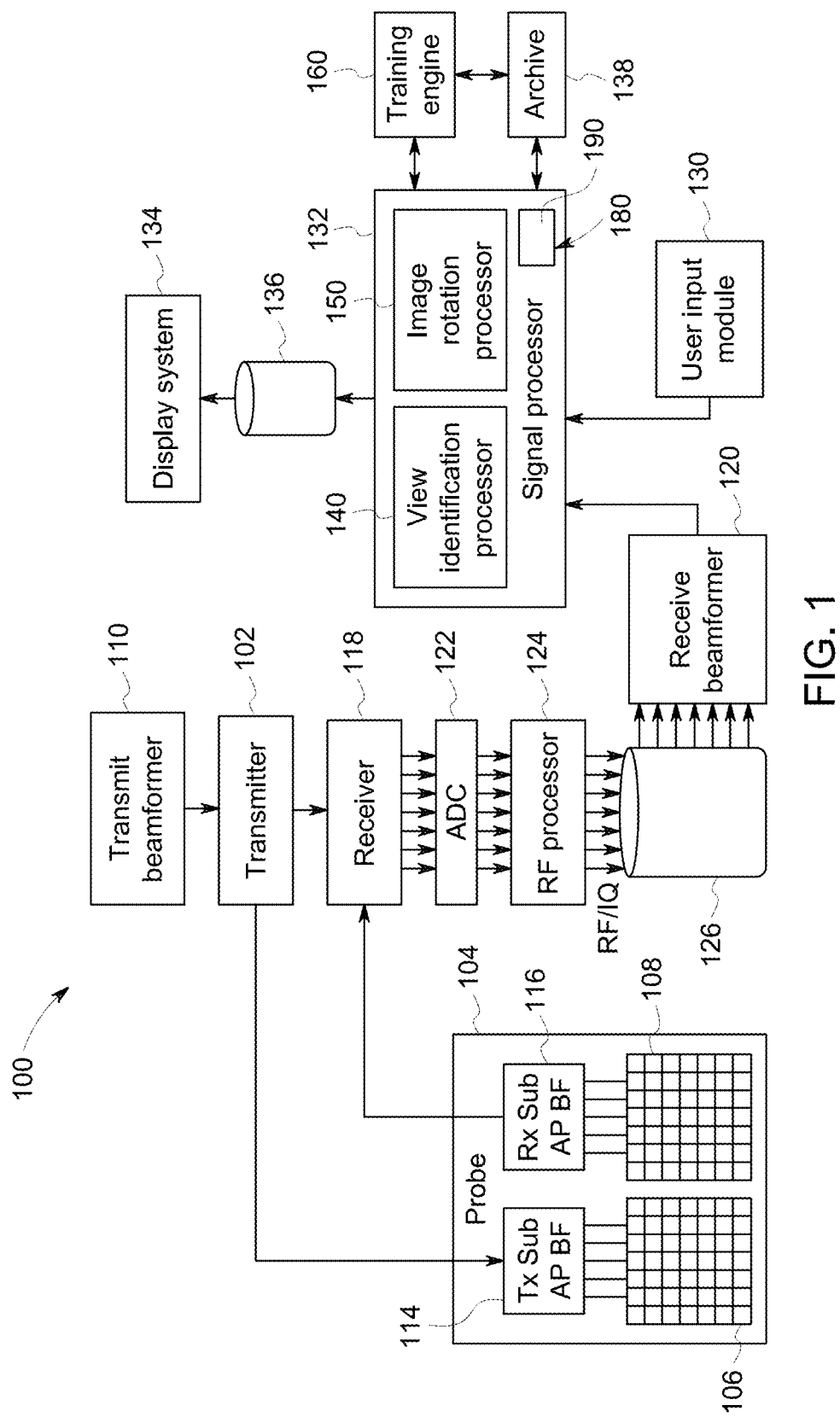
FIG. 1 is a schematic view of an ultrasound imaging system according to an embodiment of the disclosure.

Certain embodiments may be found in a method and system for acquiring standard ultrasound scan plane views. Various embodiments have the technical effect of acquiring a 3D image of the object being scanned by the probe during a detected period of inactivity of the object to provide a 3D volume map representing the position of the ultrasound probe relative to the object for presentation on a display.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1, such as those examples disclosed in US Patent Application Publication Nos. US2020/0289096, entitled Method And System For Providing Standard Ultrasound Scan Plane Views Using Automatic Scan Acquisition Rotation And View Detection, the entirety of which is hereby expressly incorporated herein by reference for all purposes.

FIG. 1 is a block diagram of an exemplary ultrasound system that is operable to acquire standard ultrasound scan plane views, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input module 130, a signal processor 132, an image buffer 136, a display system 134, a memory unit/archive 138, and a training engine 160.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure. The ultrasound probe 104 can be any suitable ultrasound probe operable to acquire ultrasound scan planes at different rotational and/or tilt angles without physically moving the ultrasound probe. In an exemplary embodiment, the ultrasound probe 104 may include a one dimensional transducer array that can be mechanically oriented in a plurality of orientations by a motor in response to instructions from the signal processor 132. In a preferred embodiment, the probe 104 includes a 2D array of ultrasound elements operable to electronically transmit ultrasonic signals and acquire ultrasound data in any orientation in three dimensional space, called a four dimensional (e4D) matrix probe. For example, the e4D ultrasound probe 104 may be the GE 4Vc-D four dimensional (4D) matrix cardiac probe. The processing of the acquired images in any steered direction can be performed partially or completely by probe-internal sub-aperture processing, by system side software beamforming, or by beamforming in hardware. In an exemplary embodiment, the acquired scan planes are either 2D images and/or thin slab images. For example, thin slab images may be acquired using multi-line acquisition (MLA) where a plurality of transmit beams are arranged spatially along a plane and multiple receive beams for each transmit beam are received orthogonal to a plane width of the transmit beams. In various embodiments, a thickness of the thin slab images may be 7 millimeters or less. The system 100 can additionally acquire 3D/volumetric ultrasound images of the anatomy or object using a similar process to that utilized for the acquisition of the slab images.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132 for image generation and presentation on the display system 134. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input module 130 may be utilized to input patient data, scan parameters, settings, select protocols and/or templates, select one or more desired standard views, provide a command for storing a displayed scan plane, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display.

In various embodiments, a protocol and/or one or more desired standard views may be selected during or at the onset of an imaging procedure in response to a directive received via the user input module 130. For example, an ultrasound operator may identify a transthoracic echocardiogram acquired at an apical window protocol at an onset of an imaging procedure via the user input module 130. The protocol may include a number of pre-defined standard views, such as a four chamber (4CH) view, a two chamber (2CH) view, an apical long axis (APLAX) view, a parasternal long axis (PLAX) view, a parasternal short axis (PSAX) view; and the like. The selected protocol may be provided via the user input module 130 to the signal processor 132 so that the signal processor 132 may apply view detection processing and acquisition rotation and/or tilt parameters. The view detection processing applied by the signal processor 132 may automatically detect each of the standard views. The acquisition rotation and/or tilt parameters may be applied by the signal processor 132 to automatically rotate and/or tilt scan plane acquisition to acquire each of the standard views once the ultrasound probe 104 is properly positioned at the apical window.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the memory unit/archive 138. The archive/memory unit 138 may be a local archive, a Picture Archiving and Communication System (PACS), or any suitable device for storing images, executable commands and functions of the image processing unit 132, and/or related information.

Figure 2:
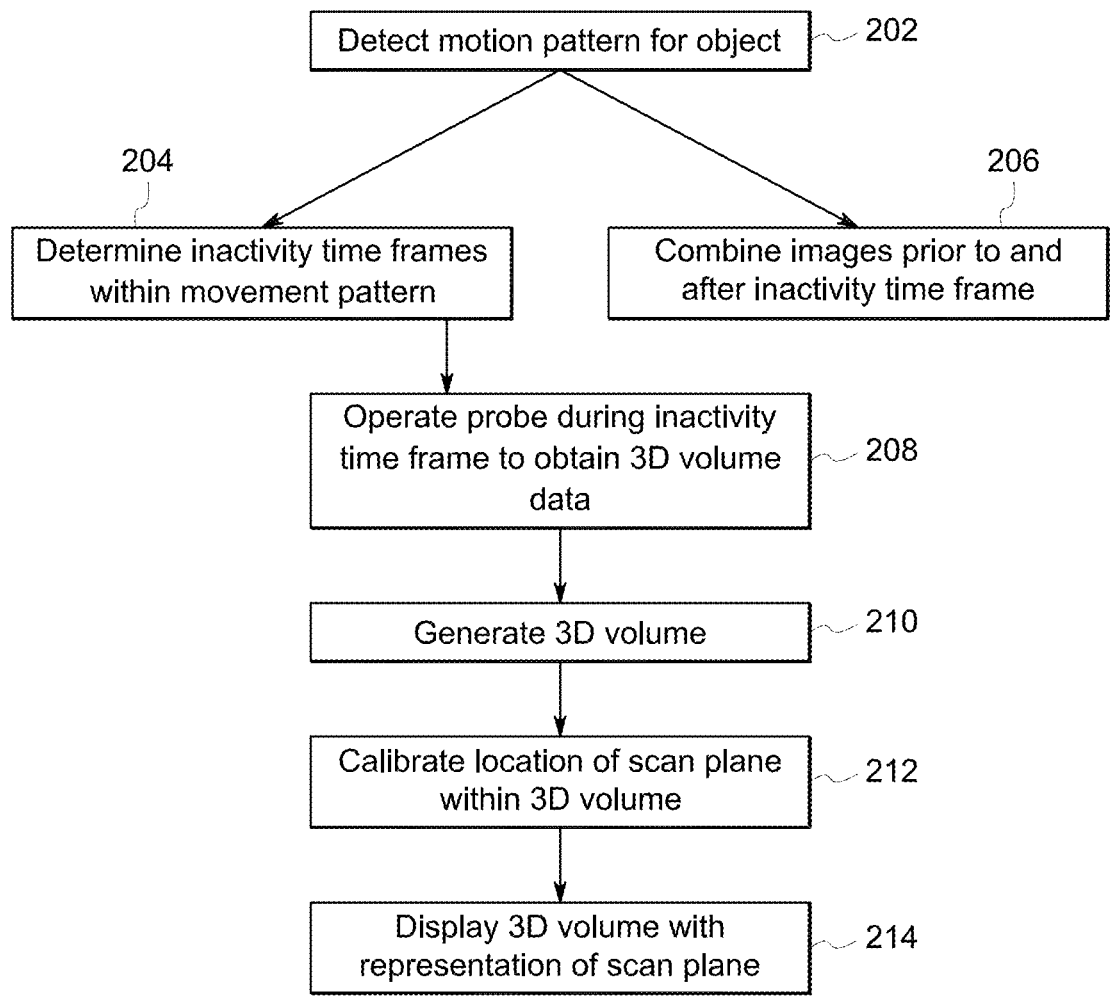
FIG. 2 a flowchart illustrating the method according to an exemplary embodiment of the present disclosure.

Referring now to FIGS. 1 and 2, the system 100 additionally includes a motion detection system 180, which can be formed as a part of the signal processor 132 or as a separate component of the system 100 that has access to the ultrasound scan data from the probe 104. In the illustrated exemplary embodiment of the method of operation 200 of the motion detection system 180 in FIG. 2, the motion detection system 180 is capable of analyzing data regarding the object being imaged that is obtained directly from the imaging system 100 and/or from a separate medical sensing and/or diagnostic system, such as an electrocardiogramatem 400 that is operably connected to the processor 132/motion detection system 180, or that is included as a component part of the motion detection system 180 for the automatic detection of QRS complexes, which are utilized to calculcate the heart rate of the patient, and then estimating the timing of the diastasis interval using by known emprical formulas, in order to determine and/or estimate a period of inactivity of the object based on a determined movement pattern of the object. The motion detection system 180 can utilize various types of data concerning the object in order to make this determination and/or estimation of the most inactive time frame(s) within the movement cycle(s) of the object imaged by the ultrasound imaging system 100, including but not limited to electrocardiograph data and/or ultrasound scan data. In one exemplary embodiment, the electrocardiograph data and/or ultrasound scan data is obtained in real time in order to determine a movement pattern of the object, and whether motion within the object being scanned has paused for a repeatable inactivity time frame. The motion detection system 180 can perform this task in any of a number of suitable manners, techniques and/or processes, and in an exemplary embodiment does so through the use of one or more of a pattern recognition algorithm, a neural network, machine learning and/or an artificial intelligence (AI) 190 forming a part of the motion detection system 180 and having executable functions/information stored on the image processor 132, within the memory unit 138, or in any other suitable location or manner for the operation of the AI application 190.

In block 202 of one exemplary embodiment of the method 200, the system 180/AI 190 initially reviews the electrocardiograph ad/or ultrasound scan data and determines if all or any relevant portions of the object being scanned have temporarily stopped moving based on the representations of the various portions of the object in the electrocardiograph data, e.g., the PR and/or ST segments of the detected electrocardiogram of a cardiac object, the detected interval between the U wave and the P wave, and/or ultrasound scan data, e.g., little or no movement of the object between successive/multiple 2D images generated by the image processor 132. More specifically, the system 180/AI 190 analyzes the object movement data, e.g., electrocardiogram and/or ultrasound scan data, in order to determine any repeating pattern of time frames within the movement cycle of the object in which the object is minimally moving or is not moving, e.g., is stationary.

For example, when object being scanned is the heart of a patient, the image processor 132 will provide 2D images from the ultrasound scan data of the heart in motion corresponding to the cardiac cycle for the heart, i.e., the motion of the heart through the systole and diastole portions of the cardiac cycle. With the ultrasound scan data for the cardiac cycle provided, the system 180/AI 190 can review the ultrasound scan data/2D images in order to locate those 2D images in which the heart is not moving/has only minimal motion. These 2D images correspond to the rest period within the cardiac cycle when the heart is inactive or moving only minimally, i.e., the portion of the cardiac cycle for the imaged heart during which diastasis occurs. This ultrasound scan data can be utilized alone by the system 180/AI 190, in combination with electrocardiograph data from an external or an internal electrocardiogramatem 400 or can use only the electrocardiograph data to make this determination.

Proceeding to block 204, the system 180/AI 190 can then use the information provided by the electrocardiography and/or image data to determine/detect the approximate length of the window/time frame for the inactivity the object, e.g., when the heart is in diastasis. During this inactivity time frame, the ultrasound scan data being obtained by the probe 104 is largely similar to the ultrasound scan data obtained both immediately prior to and after the detected time frame. As a result, the ultrasound scan data obtained via the probe 104 during the detected inactivity time frame can readily be omitted from any real time 2D images provided by the signal processor 132 as being closely duplicative of the ultrasound scan data/2D images from immediately prior to and immediately after the inactivity time frame.

Further, the ultrasound scan data/2D images from immediately prior to and immediately after the inactivity time frame can be stitched together and/or interpolated by the system 180/AI 190 in block 206 in order to provide a seamless appearance to the 2D images generated by the signal processor 132 from the ultrasound scan data and presented on the display system 134 without any significant temporal resolution loss in the displayed 2D images. In an exemplary embodiment, the system 180/AI 190 can stitch or interpolate the scan data for the ultrasound image immediately prior to the inactivity time frame with the scan data for the ultrasound image immediately following the inactivity time frame to create an inactivity time frame ultrasound image for presentation on the display system 134 during the inactivity time frame.

After determining the inactivity time frame, and after or concurrently with the stitching of the ultrasound scan data/images immediately prior to and immediately after the inactivity time frame, in block 208 the system 180/AI 190 proceeds to operate the probe 104 during the inactivity time frame to obtain a 3D volume/image 300 (FIG. 3) of the object being scanned. In an exemplary embodiment of its operation, the system 180/AI 190 can determine the inactivity time frame in a first number of movement cycles of the object, e.g., a first cardiac cycle, and can operate the probe 104 to obtain the 3D volume 300 during the inactivity time frame of a second or any subsequent movement cycle of the object.

Once obtained, the system 180/AI 190 proceeds in block 210 to use the 3D/volumetric ultrasound scan data obtained during the inactivity time frame to generate a 3D volume 300 (FIG. 3) representation of the object. In alternative embodiments, the 3D volume 300 is presented on the display system 134, but can also remain internal to the system 180/AI 190.

As the 3D volume 300 corresponds to the object being scanned, in block 212, the system 180/AI 190 can calibrate and/or determine the location of the scan plane 302 for the ultrasound image 304 within the 3D volume. With this calibration, the system 180/AI 190 can present the 3D volume 300 on the display system 134 with a representation of the actual scan plane 302 currently being obtained by the probe 104 in relation to the position of the probe 104 relative to the 3D volume 300, as well as any modification due to the current operational scan parameters, settings, protocols and/or templates employed with the probe 104.

Figure 3:
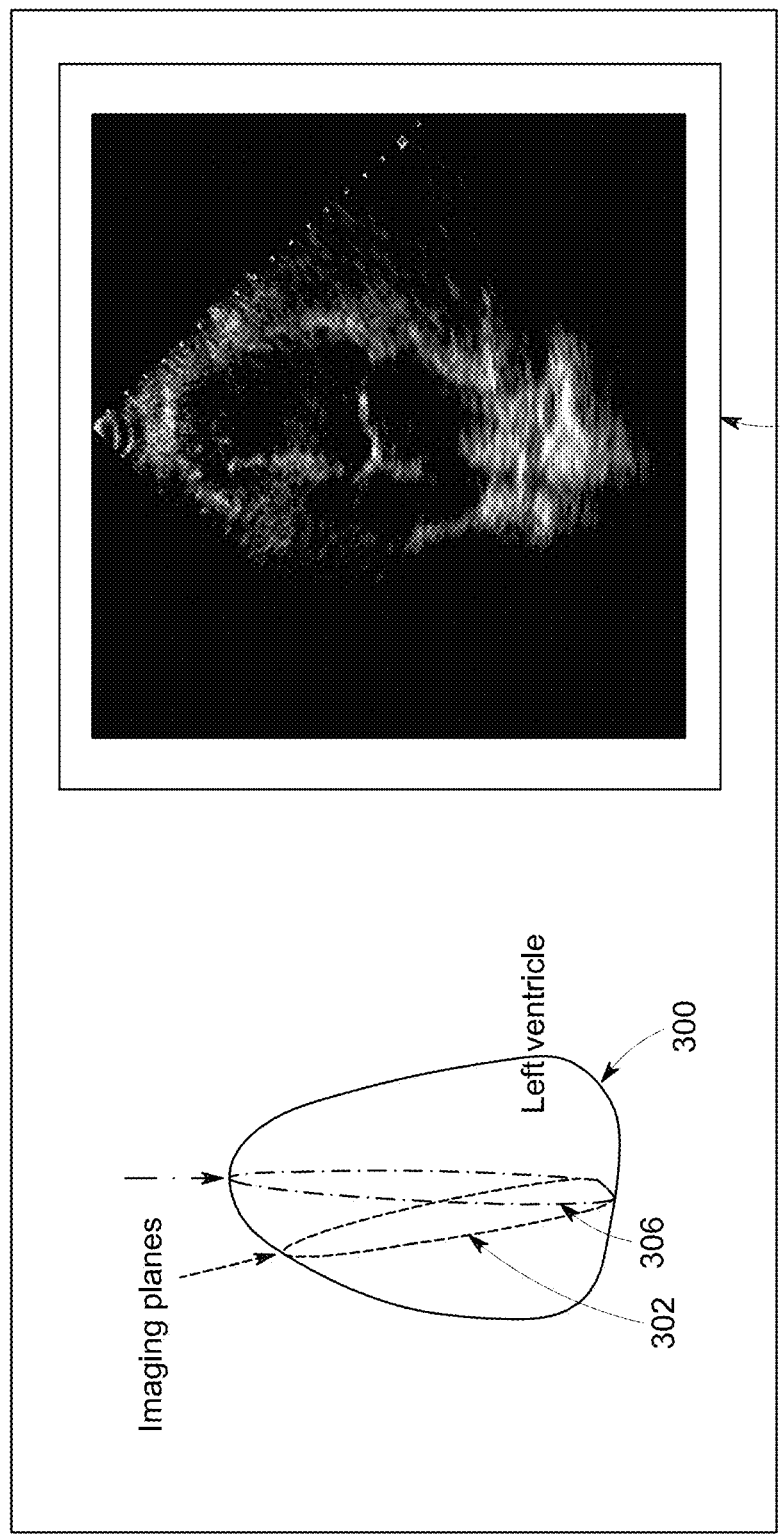
FIG. 3 is a schematic representation of a display presenting a 3D ultrasound volume map illustrating the detected position of an ultrasound probe in association with the 2D ultrasound image being obtained by the probe.

As illustrated in FIG. 3, the representation 302 of the scan plane on the 3D volume 300, such as a line or a plane intersecting the 3D volume 300, can be presented on the display 134 in an optional step of block 214 to provide the operator with a visual indication/representation of the scan plane 302 in association with the real time 2D image(s) 304 presented on the display system 134. The 3D volume 300 and scan plane representation 302 thus enable the operator to have a real time localization of the position of the displayed 2D image 304 relative to the object/3D volume being scanned, such that the operator has a visual indication of the current scan plane representation 302 relative to a desired scan plane of a standard view (which can optionally be represented on the 3D volume 300 with a separate scan plane indicator 306), or of the necessary adjustment of the position of the probe 104 relative to the object/3D volume 300 to decrease or eliminate and foreshortening in the displayed 2D image(s) 304.

The operation of the system 180/AI application 190 in blocks 208-214 can be repeated during successive cycles/during the inactivity time frames within successive cycles in order to update the representation on the display system 134 of the current scan plane representation 302 relative to the 3D volume 300 and any desired scan plane indicator 306 to provide guidance for movement of the probe 104 to the operator to the location to obtain the desired standard view of the object.

In addition, with the generation of the 3D volume 300 during the inactivity time frame, the ultrasound scan data and scan planes from multiple 2D acquisitions/image 304 of the object, e.g., heart, obtained at any of the apical, parasternal, and any other view windows, can be precisely calibrated with regard to their relative locations to one another utilizing the known locations of the scan plane representations 302 of the individual 2D images 304 relative to the one or more 3D volumes 300 that are obtained. Thus, the correlation of the scan plane representations 302/2D images 304 through the 3D volume(s) 300 enables the transformation of the ultrasound scan data from multiple views/2D images 304, and optionally in conjunction with the 3D volume(s) 300, into a single shared vector space (not shown) comprising the combined scan data from the calibrated 2D images 304 to describing the dimensions and motion of the scanned object, which in the exemplary embodiment is the heart. This vector space is a representation of an object (i.e. the heart) as a series of vectors describing the edges and other important features of the object in a common 3D coordinate system. The edges and features are extracted and combined from multiple 2D images corresponding to multiple views of the object so the vector space summarizes all known information on the object. In alternative embodiments of the system 180/AI application 190 and its operation where the 3D volume 300 is not presented in the display 134, as the 3D volume in all embodiments is stored in conjunction with the 2D image(s) 304, for subsequent measurements of the object the stored 3D volume 300 can be used to align the current 2D image(s)/ultrasound sector 304 with other/subsequent 2D image(s) 304/ultrasound sector obtained of the object using the probe 104 positioned at different positions, directions and/or angles relative to the object.

Figure 4:
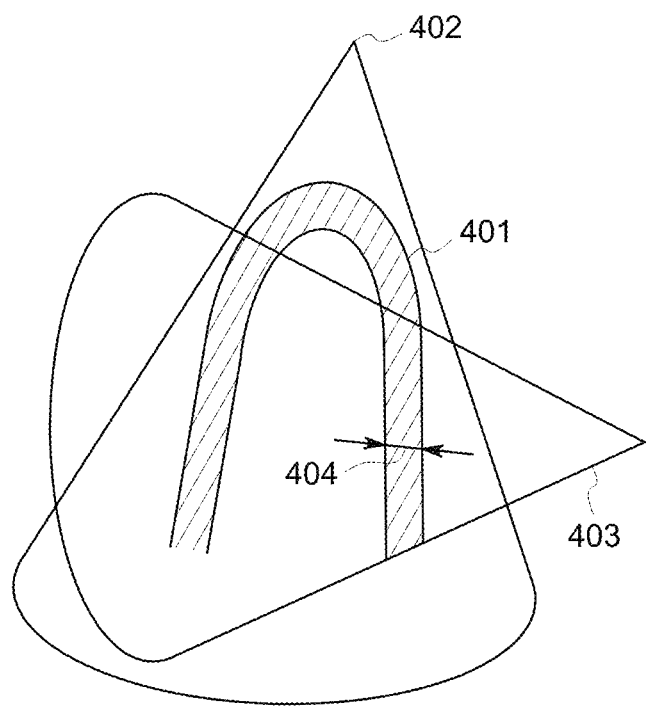
FIG. 4 is a schematic view of a vector space of a left ventricle myocardium of a heart formed by the registration of a A-4CH image of the heart and a PLAX image of the heart.

For example, with reference to FIG. 4, a vector space 401 representing a left ventricle myocardium is illustrated that is created from the alignment of an apical long axis (APLAX) ultrasound image/ultrasound sector 402 and parasternal long axis (PLAX) ultrasound image/ultrasound sector 403 using a 3D volume 300 obtained of the left ventricle myocardium. The 3D volume 300 is obtained during the inactivity period determined for the object (i.e., the diastasis of the heart) during the imaging procedure utilized for obtaining the images 402 and 403. By aligning/registering the 3D volumes 300 obtained during various diastasis periods at different image angles/positions with each other, the APLAX image 402 and the PLAX image 403 can be aligned with one another in a 3D space using the aligned 3D volumes 300. In FIG. 4, the alignment of the views 402 and 403 results in the creation of the vector space representation 401 of the left ventricle myocardium. From this vector space 401, various measurements of the object represented by the vector space representation 401 can be obtained, such as a thickness measurement 404, instead of being obtained from one of the individual ultrasound images/sectors 402 or 403, which can result in a more accurate measurement.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasound imaging system for obtaining ultrasound images of an interior of an object, the ultrasound imaging system comprising:
    an image processing unit configured to receive and process acquired ultrasound scan data to create 2D ultrasound images, the image processing unit including a motion detection system configured to detect a pattern of inactivity time frames within movement cycles of the object by locating 2D ultrasound images generated from the ultrasound scan data in which the object is not moving that define the inactivity time frame;
    a memory unit operably connected to the image processing unit;
    a display operably connected to the image processing unit to present the ultrasound images to a user; and
    an ultrasound imaging probe operably connected to the image processing unit to acquire the ultrasound scan data for use by the image processing unit to form the 2D ultrasound images and to acquire volumetric ultrasound scan data,
    wherein the motion detection system is configured to detect a pattern of one or more inactivity time frames within a first cycle of movement of the object, to operate the probe to obtain volumetric ultrasound scan data of the object using the probe during the one or more inactivity time frames within a second cycle of movement of the object corresponding to the detected pattern of one or more inactivity time frames within the first cycle of movement of the object; to generate a volumetric ultrasound image from the volumetric ultrasound scan data obtained during the one or more inactivity time frames in the second cycle; and to calibrate a location of a scan plane of the 2D ultrasound image within the volumetric ultrasound image.

2. The ultrasound imaging system of claim 1, wherein the motion detection system comprises a pattern recognition artificial intelligence.

3. The ultrasound imaging system of claim 1, wherein the motion detection system is configured to stitch the 2D ultrasound image immediately prior to the one or more inactivity time frames together with the 2D ultrasound image immediately following the one or more inactivity time frames or to interpolate scan data for the 2D ultrasound image immediately prior to the one or more inactivity time frames with scan data for the 2D ultrasound image immediately following the one or more inactivity time frames to create an inactivity time frame 2D ultrasound image.

4. The ultrasound imaging system of claim 1, wherein the volumetric ultrasound image is presented on the display in association with a representation of the 2D ultrasound image within the volumetric ultrasound image.

5. The ultrasound imaging system of claim 4, wherein the representation of the 2D ultrasound image is a representation of the scan plane of the 2D ultrasound image.

6. The ultrasound imaging system of claim 5, further comprising a representation of a desired scan plane within the volumetric ultrasound image.

7. The ultrasound imaging system of claim 1, wherein the motion detection system is configured to update the location of the scan plane of the 2D ultrasound image within the volumetric ultrasound image during subsequent inactivity time frames within subsequent movement cycles of the object.

8. The ultrasound imaging system of claim 1, wherein the motion detection system is configured to combine ultrasound scan data from multiple 2D ultrasound images calibrated with the volumetric ultrasound image into a shared vector space representation of the object.

9. The ultrasound imaging system of claim 1, wherein the volumetric ultrasound image is presented on the display in association with a representation of a scan plane of the 2D ultrasound image and a representation of a desired scan plane to prevent foreshortening in the 2D ultrasound image.

10. A method for determining a location of a scan plane for an ultrasound image of an object, the method comprising the steps of:
    providing an ultrasound imaging system comprising:
        an image processing unit configured to receive and process acquired ultrasound scan data to create 2D ultrasound images, the image processing unit including a motion detection system configured to detect a pattern of inactivity time frames within movement cycles of the object;
        a memory unit operably connected to the image processing unit;
        a display operably connected to the image processing unit to present the ultrasound images to a user;
        an ultrasound imaging probe operably connected to the image processing unit to acquire the ultrasound scan data for use by the image processing unit to form the ultrasound images,
        wherein the motion detection system is configured to detect a movement pattern of one or more inactivity time frames within the first cycle of movement of the object by locating 2D ultrasound images generated from the ultrasound scan data in which the object is not moving, to operate the probe to obtain volumetric ultrasound scan data of the object at a start of the one or more inactivity time frames within a second cycle of movement of the object as determined by the detected pattern of one or more inactivity time frames within the first cycle of movement of the object; to stop operation of the probe to obtain volumetric ultrasound scan data of the object at an end of the one or more inactivity time frames within a second cycle of movement of the object as determined by the detected pattern of one or more inactivity time frames within the first cycle of movement of the object; and to form a volumetric ultrasound image of the object, and to calibrate a location of the scan plane of the 2D ultrasound image within the volumetric ultrasound image;
    obtaining 2D ultrasound scan data using the probe;

determining the movement pattern of the object for the first cycle of movement of the object from the 2D ultrasound scan data;

determining one or more inactivity time frames within the movement pattern of the object for the first cycle of movement;

operating the probe to obtain volumetric ultrasound scan data of the object using the probe at a start of the one or more inactivity time frames within the second cycle of movement of the object as determined by the detected pattern of one or more inactivity time frames within the first cycle of movement of the object;

stopping operation of the probe to obtain volumetric ultrasound scan data of the object at an end of the one or more inactivity time frames within the second cycle of movement of the object as determined by the detected pattern of one or more inactivity time frames within the first cycle of movement of the object;

generating a volumetric ultrasound image of the object from the volumetric ultrasound scan data; and calibrating a location of the scan plane of the 2D ultrasound image within the volumetric ultrasound image.

11. The method of claim 10, further comprising the steps of:

presenting the volumetric ultrasound image on the display after calibrating the location of the scan plane of the 2D ultrasound image within the volumetric ultrasound image; and presenting a representation of the location of the scan plane of the 2D ultrasound image within the volumetric ultrasound image.

12. The method of claim 11, further comprising the step of presenting a representation of a location of a desired scan plane within the volumetric ultrasound image.

13. The method of claim 11, further comprising the step of:

stitching the 2D ultrasound image immediately prior to the start of the one or more inactivity time frames within the second cycle of movement together with the 2D ultrasound image immediately following the end of the one or more inactivity time frames within the second cycle of movement; or interpolating the scan data for the 2D ultrasound image immediately prior to the start of the one or more inactivity time frames within the second cycle of movement with the scan data for the 2D ultrasound image immediately following the end of the one or more inactivity time frames within the second cycle of movement to create an inactivity time frame 2D ultrasound image.

14. The method of claim 11, further comprising the step of updating the location of the scan plane of the 2D ultrasound image within the volumetric ultrasound image during subsequent one or more inactivity time frames within subsequent movement cycles of the object.

15. The method of claim 11, further comprising the step of combining ultrasound scan data from multiple 2D ultrasound images calibrated with the volumetric ultrasound image into a shared vector space representation of the object.

16. A method for determining a location of a scan plane for a 2D ultrasound image of a heart the method comprising the steps of:

providing an ultrasound imaging system comprising:
an image processing unit configured to receive and process acquired ultrasound scan data to create 2D ultrasound images, the image processing unit including a motion detection system configured to detect a pattern of diastasis time frames within cardiac cycles of the heart;
a memory unit operably connected to the image processing unit;
a display operably connected to the image processing unit to present the 2D ultrasound images to a user;
an ultrasound imaging probe operably connected to the image processing unit to acquire the ultrasound scan data for use by the image processing unit to form the 2D ultrasound images and to acquire volumetric ultrasound scan data to form a 3D ultrasound image,
wherein the motion detection system is configured to detect a pattern of diastasis time frames within the first cardiac cycle of the heart by locating 2D ultrasound images generated from the ultrasound scan data in which the object is not moving, to operate the probe to obtain volumetric ultrasound scan data of the heart at a start of the diastasis time frame within a second cardiac cycle of the heart; to stop operation of the probe to obtain volumetric ultrasound scan data of the heart at an end of the diastasis time frame within the second cardiac cycle of the heart; to form a 3D ultrasound image of the heart with the volumetric ultrasound scan data, and to calibrate a location of the scan plane of the 2D ultrasound image within the 3D ultrasound image;

obtaining 2D ultrasound scan data using the probe;

determining a movement pattern of the heart for the first cardiac cycle of the heart;

determining a diastasis time frame within the movement pattern of the first cardiac cycle of the heart;

obtaining volumetric ultrasound scan data using the probe during the determined diastasis time frame in the second cardiac cycle of the heart;

obtaining 2D ultrasound scan data using the probe subsequent to the end of the determined diastasis time frame in the second cardiac cycle of the heart;

generating a 3D ultrasound image of the heart from the volumetric ultrasound scan data; and calibrating a location of the scan plane of the 2D ultrasound image within the 3D ultrasound image.

17. The method of claim 16, further comprising the steps of:

presenting the 3D ultrasound image on the display after calibrating the location of the scan plane of the 2D ultrasound image within the 3D ultrasound image; and presenting a representation of the location of the scan plane of the 2D ultrasound image within the 3D ultrasound image.

18. The method of claim 16, further comprising the step of presenting a representation of a location of a desired scan plane to eliminate foreshortening within the 3D ultrasound image.

19. The method of claim 16, further comprising the step of updating the location of the scan plane of the 2D ultrasound image within the 3D ultrasound image during subsequent diastasis time frames within subsequent cardiac cycles of the heart.

* * * * *